(12) United States Patent
Navot et al.

(10) Patent No.: US 6,335,165 B1
(45) Date of Patent: Jan. 1, 2002

(54) METHODS AND KITS FOR CHARACTERIZING GC-RICH NUCLEIC ACID SEQUENCES

(75) Inventors: Nir Navot, Rosh Haayin; Martine Lederkremer, Shoham, both of (IL)

(73) Assignee: Gamidagen Ltd., Ashdod (IL)

( * ) Notice: Subject to any disclaimer, the term of this patent is extended or adjusted under 35 U.S.C. 154(b) by 0 days.

(21) Appl. No.: 09/236,097

(22) Filed: Jan. 25, 1999

(51) Int. Cl.[7] .......................... C12Q 1/68; C12P 19/34; C07H 21/02
(52) U.S. Cl. ........................ 435/6; 435/91.2; 536/23.1; 935/77; 935/78; 935/82
(58) Field of Search ................... 435/91.2, 6; 536/23.1; 935/77, 78, 82

(56) References Cited

U.S. PATENT DOCUMENTS 5,650,277 A  *  7/1997  Navot et al. .................... 435/6
5,658,764 A       8/1997  Pergolizzi et al. ......... 435/91.2

FOREIGN PATENT DOCUMENTS

WO          98/1352       2/1998    ............ C12Q/1/68

OTHER PUBLICATIONS

Guldberg et al, "Detection of Mutations in GC–Rich DNA by Bisulphite Denaturing Gradient Gel Electrophoresis", *Nucleic Acids Research*, 26(6): 1548–1549, 1998.

Henke et al, "Betaine Improves the PCR Amplification of GC–Rich DNA Sequences", *Nucleic Acids Research*, 25(19): 3957–3958, 1997.

Schuchard et al, "Two–Step "Hot" PCR Amplification of GC–Rich Avian c–myc Sequences", *Biotechniques*, 14(3): 390–394, 1993.

Turner, et al, "Use of Deoxyinosine in PCR to Improve Amplification of GC–Rich DNA", *Biotechniques*, 19(1): 48–52, 1995.

Passadore et al., "Differential Effects of Distamycin Analogues on Amplification of Human Gene Sequences by Polymerase–Chain Reaction", *Biochem J.,* 308: 513–519, 1995.

Larsen et al, "High–Throughput Analysis of Fragile X $(CGG)_n$ Alleles in the Normal and Premutation Range for PCR Amplification and Automated Capillary Electrophoresis", *Hum Genet,* 100: 564–568, 1997.

Nyren et al, "Detection of Single–Base Changes Using a Bioluminometric Primer Extension Assay", *Analytical Biochemistry,* 244: 367–373, 1997.

Nakahara et al, Inosine 5'–Triphosphate can Dramatically Increase the Yield of NASBA Products Targeting GC–Rich and Intramolecular Base–Paired Viroid RNA, *Nucleic Acids Research,* 26(7): 1854–1855, 1998.

Nyren et al, Solid–Phase DNA Minisequencing by an Enzymatic Luminometric Inorganic Pyrophosphate Detection Assay, *Analytical Biochemistry,* 208: 171–175, 1993.

Ronaghi et al, "Real–Time DNA Sequencing Using Detection of Pyrophosphate Release", *Analytical Biochemistry,* 242: 84–89, 1996.

Ĉuljkoví˝ et al, "Improved Polymerase Chain Reaction Conditions for Quick Diagnostics of Huntington Disease", *Brain Research Protocols,* 2: 44–46, 1997.

* cited by examiner

*Primary Examiner*—Kenneth R. Horlick
*Assistant Examiner*—Joyce Tung

(57) ABSTRACT

Methods and kits of characterizing a GC rich region of a nucleic acid of interest are provided. One method is effected by (a) contacting the nucleic acid of interest with an agent that modifies cytosine or guanine residues into residues complementary to adenine or thymine for obtaining a modified nucleic acid in which the cytosine or guanine residues are replaced by the residues complementary to adenine or thymine; (b) amplifying the modified nucleic acid by amplification primers being hybridizable with the modified nucleic acid and being designed for directing amplification of at least a portion of the modified nucleic acid, for obtaining an amplification product corresponding to the GC rich region; and (c) determining the size of the amplification product, thereby characterizing the GC rich region of the nucleic acid of interest.

23 Claims, 2 Drawing Sheets

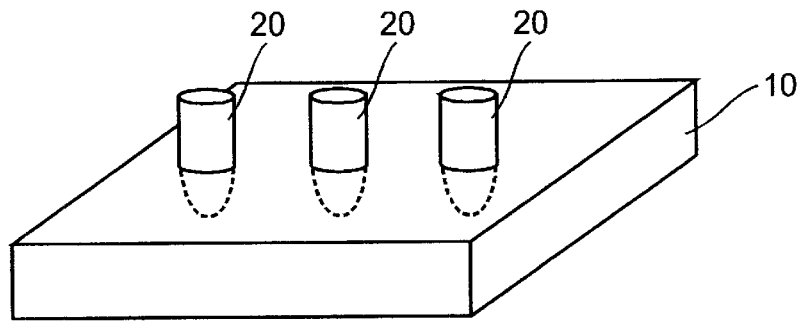

Fig. 1

```
SEQ ID NO:7
CCAGACCAGACACCCCCTCCCGCGGAATCCCAGAGAGGCCGAACTGGGATAACCGGA
TGCATTTGATTTCCCACGCCACTGAGTGCACCTCTGCAGAAATGGGCGTTCTGGCCC
TCGCGAGGCAGTGCGACCTGTCACCGCCCTTCAGCCTTCCCGCCCTCCACCAAGCCC
GCGCACGCCCGGCCCGCGCGTCTGTCTTTCGACCCGGCACCCGGCCGGTTCCCAGC
AGCGCGCATGCGCGCGCTCCCAGGCCACTTGAAGAGAGAGGGCGGGGCCGAGGGGCT
GAGCCCGCGGGGGGAGGGAACAGCGTTGATCACGTGACGTGGTTTCAGTGTTTACAC
CCGCAGCGGGCCGGGGGTTCGGCCTCAGTCAGGCGCTCAGCTCCGTTTCGGTTTCAC
TTCCGGTGGAGGGCCGCCTCTGAGCGGGCGGCGGGCCGACGGCGAGCGCGGGCGGCG
GCGGTGACGGAGGCGCCGCTGCCAGGGGCGTGCGGCAGCGCGGCGGCGGCGGCGGC
GGCGGCGGCGGCGGAGGCGGCGGCGGCGGCGGCGGCGGCGGCGGCTGGGCCTCGAGC
GCCCGCAGCCCACCTCTCGGGGGCGGGCTCCCGGCGCTAGCAGGGCTGAAGAGAAGA
TGGAGGAGCTGGTGGTGGAAGTGCGGGCTCCAATGGCGCTTTCTACAAGGTACTTG
GCTCTAGGGCAGGCCC
```

Fig. 2

SEQ ID NO:8:
UUAGAUUAGAUAUUUUUTUUUGUGGAAUUUUAGAGAGGUUGAAUTGGGAUAAUU
GGAUGUAUUUGAUUUUUAUGUUAUGAGUGUAUUUUUGUAGAAAUGGGUGUUU
UGGUUUUGUGAGGUAGUGUGAUUUGUAUUGUUUUUAGUUUUUUUGUUUUUU
AUUAAGUUUGUGUAUGUUUGGUUUGUGUGUUUGUUUUUGAUUUGGUAUUUUGG
UUGGUUUUAGUAGUGUGUAUGUGUGUGUUUUAGGUUAUUGAAGAGAGGG
UGGGGUUGAGGGGUUGAGUUUGUGGGGGGAGGGAAUAGUGUUGAUAUGUGAUG
UGGUUUAGUGUUUAUAUUUGUAGUGGGUUGGGGGUUGGUUUAGUUAGGUGU
UUAGUUUGUUUGGUUUAUUUUGGUGGAGGGUUGUUUUGAGUGGGUGGUG
                       PFX52U TggTggTgATggAggTgT (SEQ ID NO:9)
GGUUGAUGGUGAGUGUGGGUGG<u>UGGUGGUGAUGGAGGUGUUGUGUUAGGGGGU
GUGUGGUAGUGU<i>GCUGGUGGUGGUGGUGGUGGUGGUGGUGGAGGUGGUGGUGGU
GGUGGUGGUGGUGGUGGU</i>UGGGUUUGAGUGUUUGUAGUUUAUUUUGGGGGU</u>
       PFX52L  CATCCCAACTTCTCTTCTACCT (SEQ ID NO 10)
GGGUUUUUGGUGU<u>UAGUAGGGUUGAAGAGAAGAUGGAGGAGUGGUGGUGGAAG</u>
UGUGGGGUUUUAAUGGUGUUUUUAUAAGGUAUUUGGUUUUAGGGUAGGUUU

Fig. 3

SEQ ID NO:11
GGGUUUGUUUUAGAGUUAAGUAUUUUGUAGAAAGUGUUAUUGGAGUUUUG
UAUUUUUAUUAUUAGUUUUUUAUUUUUUUUUAGUUUUGUUAGUGUUGG
           PFX30U   TgggTTgTgggTgTTTgAg (SEQ ID NO: 12)
GAGUUUGUUUUUGAGAGG<u>TGGGUUGUGGGUGUUUGAGGUUUA<i>GUUGUUGU
UGUUGUUGUUGUUGUUGUUGUUUUUGUUGUUGUUGUUGUUGUUGUUGUUG
UUGU</i>GUUCUUGUAUGUUUUUGGUAGUGGUGUUUUGUAUGUUGUUGU</u>
UUGUGUUGUUGUGGUUUGUUGUUUGUUAGAGGUGGUUUUUAUUUGGA
AGUGAAAUUGAAAUGGAGUGAGUGUUUGAUUGAGGUUGAAUUUUUGGUU
UGUUGGGGUGUAAAUAUUGAAAUUAUGUUAUGUGAUAAUGUUGUUUUU
UUUUUUUGUGGGGUUAGUUUUUGGUUUUGUUUUUUUUUUAAGUGGUU
UGGGAGUGUGUGUAUGUGUGUGUUGGGAAUUGGUUGGGGUGUUGGGUUG
      CTATCTACACACCCAACCCAC PFX30L (SEQ ID NO:13)
AAA<u>GAUAGAUGUGUGGGUUGGGUG</u>UGUGUGGGUUGGUGGAGGGUGGGAA
GGUGAAGGGUGGUGAUAGGUUGUAUUGUUUGUGAGGGUUAGAAUGUUU
AUUUUGUAGACGUGUAUUUAGUGGUGUGGGAAAUAAAUGUAUUUGGUU
AUUUUAGUUUGGUUUUUUUGGGAUUUUGUGGGAGGGGGUGUUUGGUUUGG

Fig. 4

METHODS AND KITS FOR CHARACTERIZING GC-RICH NUCLEIC ACID SEQUENCES

FIELD AND BACKGROUND OF THE INVENTION

The present invention relates to methods and kits for characterizing GC rich nucleic acid sequences. More particularly, the present invention relates to methods and kits for amplification, size determination and sequencing of GC rich nucleic acid sequences. Most particularly, the present invention relates to methods and kits for amplification, size determination and sequencing of GC rich nucleic acid sequences, such as the trinucleotide repeats in the FMRI gene causing the Fragile X syndrome, and other genes.

Triple Repeat Mutations

Trinucleotide repeats are the sites of mutation in several heritable human disorders. These repeats are usually GC rich (e.g., over 65% GC) and are highly polymorphic in the normal population. Fragile X syndrome and myotonic dystrophy (DM) are examples of diseases in which premutation alleles cause little or no disease in the individual, but give rise to significantly amplified repeats in affected progeny. This newly identified mechanism of penetration has so far been identified in the following diseases: Fragile X syndrome (FRAXA); spinal and bulbar muscular atrophy (SMBA); myotonic dystrophy (DM); Huntington's disease (HD); spinocerebrellar ataxia type 1 (SCA1) fragile XE (E site) mental retardation (FRAXE-MR) and dentatorubral pallidoluysian atrophy (DRAPLA). Triplet repeats are found both near to, and within additional genes, as one can learn from screening data bases of gene sequences. It is probable that in the future it will be found that the same penetration mechanism is responsible for the existence of additional genetic diseases.

Of the seven diseases listed hereinabove, Fragile XA is the most common. It is a recessive X-linked genetic disorder (therefore affecting mostly males) with an incomplete penetrance. The syndrome is difficult to diagnose in newborns and the disease features accumulate slowly with age. Developmental delay and mental retardation are the predominant clinical features of Fragile X syndrome. Mental retardation varies from extreme to borderline with the average IQ in the moderately retarded range. Female patients are more mildly affected, with few somatic signs and generally the retardation falls in to the mild—borderline category. Fragile-XA is one of the most common forms of mental retardation. It is the most common cause (one in 1500 males and one in 2500 females) of mental retardation from a single gene defect. It is also one of the commonest heritable disorders and the most common familial, heritable mental retardation. Furthermore, as the Fragile XA disease appears in all ethnic groups studied so far, it may be considered one of the most common single-gene disorders found in humans.

Fragile XA is characterized by an incomplete penetrance, consequently (i) some males are normal transmitting males' (NTMs); They are clinically normal, but their positions in the genetic pedigree makes them obligate carriers of the mutated allele. (ii) About a third of the carrier women (heterozygotes) exhibit slight symptoms of mental disturbances. The gene responsible for the syndrome was located to chromosomal position Xq27.3. Once it was cloned, it was found that within the gene there is a (CGG)n repeat that is highly polymorphic in the number (n) of repeats. This sequence is located in the 5' non-translated region of the gene. A survey conducted among healthy individuals and among individuals who suffer from the syndrome has shown that the number of triplet repeats of the sequence CGG in said polymorphic locus in the first group (normal individuals) is lower than the number of such repeats in the second group (that suffers from the syndrome). While the number of CGG repeats that characterizes X chromosomes derived from healthy individuals is low, e.g., 6–52; the number of repeats in carriers is medium, e.g., 50–200; and the number of triplet repeats in individuals who suffer from the syndrome is high, e.g., 230–1000.

It was also found that when the number of CGG repeats in the FMR1 gene increases over 230, the DNA in the 5' region of the gene is characterized by an abnormal number of methylated cytosine residues. This methylation covers also the promoter region of the gene and therefore causes its failure to replicate and the lack of expression of the FMR1 protein. This lack of expression and the changes in structure and organization of the DNA are most probably the direct molecular cause for the phenotype associated with the fragile XA syndrome (Caskey et al., Science, 1992, 256 (5058):784–9; Pieretti et al., Cell, 1991, 66(4):817–22; and Annemieke, Cell, 1991, 65:905–914.

NTMs carry numbers of CGG repeats outside the range of normal and below those found in affected males. Such males transmit the repeats to their progeny with relatively small changes in the number of repeats. On the other hand, females who carry similar premutation alleles are prone to bear progeny (male or female) with large expansion of the repeats region. Thus, large CGG amplification associated with fragile XA syndrome appears to be predominantly a female meiotic event. See, Caskey et al. Science, 1992, 256:784–789.

Many fragile XA diseased individuals were found to be mosaic with respect to the number of the CGG trinucleotide repeats characterizing different cells in their body, a phenomenon indicating somatic instability of expanded repeats.

Instability, characterized by expansion of trinucleotide repeats, is observed also in DM, HD, FRAXE, DRPLA and SCA1 pedigrees. As opposed to FRAXA, DM and FRAXE high risk alleles can expand to similar extent through both male and female meioses and, to the best of our knowledge, somatic mosaicism has not yet been observed in DM and FRAXE patients. High risk alleles have yet to be found for HD and DRPLA, that is, alleles of these diseases either cause or do not cause the disease. Nevertheless, HD repeats are also unstable in more than 80% of meiotic transmissions; on the other hand, they are characterized by increasing, or alternatively, decreasing number of repeats with the largest increase occurring in paternal transmission (Duyao. et al. Nature Genetics, 1993, 4:387–392), whereas DRPLA alleles have a tendency to increase in size along generations. See, Nagafuchi et al. Nature Genetics, 1994, 6:14–18; Koide et al. Nature Genetics, 1994, 6:9–13.

Attempts to correlate the size of trinucleotide repeat mutations and the severity of the associated genetic diseases were made for Fragile XA syndrome, Myotonic Dystrophy, Dentatorubral Pallidoluysian Atrophy and Spinocerebellar Ataxia Type 1.

For Fragile XA, as expected, median IQ score was significantly lower for females carrying a fully expanded mutation (above 230 repeats) than for females carrying a premutation (50–200 repeats) on one of their X chromosomes. On the other hand, no significant relationship was found between IQ score and number of CGG repeats, see, Taylor et al. JAMA, 1994, 271:507–514. Nevertheless, it was found that prenatal DNA studies of the number of trinucleotide repeats characterizing Myotonic Dystrophy alleles can improve the estimation of clinical severity; and that the number of CAG trinucleotide repeats in Spinocerebellar Ataxia Type 1 and Dentatorubral Pallidoluysian atrophy is correlated with increased progression of the disease (Nagafuchi et al. Nature Genetics, 1994, 6:14–18; Koide et al. Nature Genetics, 1994, 6:9–13; Orr et al. Nature Genetics, 1993, 4:221–226).

Attempts to correlate between the size of trinucleotide repeat mutations and the age of onset of Huntington's Disease resulted in finding a reverse correlation confined to the upper range of trinucleotide repeat numbers (ca. 60–100 repeats), see Andrew S. E. et al. (1993) Nature Genetics, 4:398–403.

Furthermore, for Spinocerebellar Ataxia Type 1 and Dentatorubral Pallidoluysian Atrophy (Nagafuchi S. et al. (1994) Nature Genetics, 6:14–18; Koide R. et al. (1994) Nature Genetics, 6:9–13), a direct correlation between the number of the (CAG)n trinucleotide repeats expansion and earlier ages of onset was found.

Amplification of GC-rich Sequences

In most cases triple repeats are GC-rich sequences, containing 65–100% G or C nucleotides in each strand. Other sequences of genes and other regions in genomes of various organisms are also known to include high G and C nucleotides.

As used herein in the specification and in the claims section below, a GC-rich sequence is defined to include above 50%, between 50% and 60%, above 60%, between 60% and 70%, above 70%, between 70% and 80 %, above 80%, between 80% and 90%, above 90%, between 90% and 100%, or 100% G or C nucleotides in both strands. The length of such a sequence can range from 3 base pairs to 50,000 base pairs or more. In many cases, the length of such a sequence is between tens (10–99) of base pairs to hundreds (100–999) or thousands (1000–9,999) of base pairs.

It is known to be difficult to amplify GC rich DNA sequences using conventional amplification conditions, such as conventional polymerase chain reaction (PCR) using *Thermophilus aquaticus* (Taq) DNA polymerase or equivalents. Several prior art methods have already been suggested and are presented herein.

Larsen et al. (Hum Genet, 1997, 100(5–6):564–8) teaches a method a method for analysis of the FRAXA (CGG)n region in the normal and premutation range. The method is based on polymerase chain reaction (PCR) amplification of DNA extracted from whole blood or eluted from dried blood spots on filter paper, followed by automated capillary electrophoresis and detection by multicolour fluorescence. As indicated by the authors, this method suffers severe limitations. First, it is not at all effective in amplifying full-mutation alleles. Second, due to the capillary electrophoresis procedure, it is cumbersome and time consuming.

Passadore et al. (Biochem J, 1995, 308(Pt 2):513–9) teach the use of distamycin and five distamycin analogs in polymerase-chain reaction (PCR). It is shown that the use of such nucleotide analogs improves yields in some but not all cases.

Similarly, U.S. Pat. No. 5,658,764 to Pergolizzi et al. teaches a method for amplifying and detecting specific GC-rich nucleic acid sequences contained in a nucleic acid or in a mixture of nucleic acids, which includes treating a separate nucleic acid containing the specific sequence with a molar excess of primers and a polymerase and extending the primers in the presence of dATP, dCTP, TTP, and an analogue of dGTP, such as 7-Deaza-2' deoxyguanosine triphosphate. The use of a dGTP analogue is limiting because one needs to use a highly thermostable DNA polymerase such as Pfu, which is cost ineffective, and the size of the amplified fragment is relatively restricted, making this method not useful for example, for amplification of pre-mutated or mutated alleles of the FMR1 gene which cover from 600 bp up to 6 kb).

Still similarly, Turner et al. (Biotechniques, 1995, 19(1): 48–52) teaches the use of deoxyinosine in PCR to improve amplification of GC-rich DNA.

Yet similarly, Nakahara et al. (Nucleic Acids Res, 1998, 26(7):1854–1856) teach that inosine 5'-triphosphate increases the yield of nucleic acid sequence-based amplification (NASBA) products targeting GC-rich and intramolecular base-paired viroid RNA.

Condorelli et al. (Clin Genet, 1996, 50(5):366–371) teaches that amplification across CGG repeats can be inefficient and unreliable due to their 100% G+C base composition and the use of the exonuclease-deficient Pfu polymerase for amplification and detection of the CGG repeats at the FRAXA. Pfu, however, is known to be cost-ineffective. In addition, in many cases, the use of improved MetaPhor gel electrophoretic separation was required to detect amplification bands over smears.

Guldberg et al. (Nucleic Acids Research, 1998, 26(6): 1548–1549) teaches the detection of mutations in GC-rich DNA by bisulfite denaturing gradient gel electrophoresis (DGGE) in combination with PCR and 'GC-clamping'. DGGE, however, is cumbersome, requires high calibration and highly skilled personnel for operation and is therefore limiting.

Schuchard et al. (Biotechniques, 1993, 14(3):390–394) teaches a two-step cycle PCR method, termed "hot PCR, for amplification of GC-rich DNA sequences. Using this method short sequences containing about 75% G+C were amplifyable. The two-step cycle that has been developed employs a 94° C. denaturation step and an annealing-elongation step between 70° C. and 80° C., with or without formamide. This method fails to efficiently amplify sequences having higher GC content.

Henke et al. (Nucleic Acids Res, 1997, 25(19): 3957–3958) teaches the use of betaine to improve the PCR amplification of GC-rich DNA sequences by reducing the formation of secondary structure caused by GC-rich regions.

Culjkovic et al. (Brain Res Brain Res Protoc, 1997, 2(1):44–46) teach that circumventing a GC rich region present close to the HD gene by primer selection improves PCR amplification of the CAG trinucleotide repeats thereof.

Sequencing of GC-rich Sequences

Similar difficulties and similar methods were developed over the years for the sequencing of GC rich sequences by conventional dideoxy nucleotides based sequencing reactions. Thus, nucleotide analogs producing lower melting temperatures and reagents that either lower the melting temperature and/or stabilize single stranded DNA as such were employed in sequencing reactions in an attempt to sequence GC rich sequences.

Gel Electrophoresis-free DNA Sequencing

WO9813523A1 to Nyren, Ronaghi et al. (Science, 1998, 281(5375):363, 365, Nyren et al. (Anal Biochem, 1997, 244(2):367–373) Ronaghi et al. (Anal Biochem, 1996, 242 (1):84–9) and Nyren et al. (Anal Biochem, 1993, 208(1): 171–175), all of which are incorporated by reference as if fully set forth herein, teach a method of identifying a base at a target position in a single-stranded sample DNA sequence wherein an extension primer, which hybridizes to the sample DNA immediately adjacent to the target position is provided and the sample DNA and extension primer are subjected to a polymerase reaction in the presence of a deoxynucleotide or dideoxynucleotide, whereby the deoxynucleotide or dideoxynucleotide will only become incorporated and release pyrophosphate (PPi) if it is complementary to the base in the target position, any release of PPi being detected enzymatically, different deoxynucleotides or dideoxynucleotides being added either to separate aliquots of sample-primer mixture or successively to the same sample-primer mixture and subjected to the polymerase reaction to indicate which deoxynucleotide or dideoxynucleotide is incorporated, characterized in that, the PPi-detection enzyme(s) are included in the polymerase reaction step and in that in place of deoxy- or dideoxy adenosine triphosphate (ATP) a dATP or ddATP analogue is used which is capable of acting as a substrate for a polymerase but incapable of acting as a substrate for said PPi-detection enzyme. The method advantageously permits large-scale non-electrophoretic solid phase DNA sequencing, which allows for continuous determination of the progress of the polymerization reaction with time.

Thus, an approach for real-time DNA sequencing without the need for electrophoresis has been developed. The approach relies on the detection of DNA polymerase activity by an enzymatic luminometric inorganic pyrophosphate (PPi) detection assay (ELIDA) (Nyren, Anal Biochem, 1987, 167:235–238). The PPi formed in the DNA polymerase reaction is converted to ATP by ATP sulfurylase and the ATP production is continuously monitored by the firefly luciferase. In the sequencing procedure, immobilized single-stranded template is used in a repeated cycle of deoxynucleotide extension. Real-time signals in the ELIDA, proportional to the amount of incorporated nucleotide, were observed when complementary bases were incorporated. An increased signal-to-noise ratio was obtained by substitution of deoxyadenosine alpha-thiotriphosphate (dATP alpha S) for the natural deoxyadenosine triphosphate, dATP alpha S is efficiently used by the DNA polymerase, but is not recognized by the luciferase. The possibility for parallel processing of many samples in an automated manner is discussed in the above recitations.

PCT/U.S.90/06178 (WO 91/06678), which is incorporated by reference as if fully set forth herein, teaches an instrument and method to determine the nucleotide sequence in a DNA molecule without the use of a gel electrophoresis step. The method uses an unknown primed single stranded DNA sequence which is immobilized or entrapped within a chamber with a polymerase so that the sequentially formed DNA can be monitored at each addition of blocked nucleotide by measurement of the presence of an innocuous marker on specified deoxyribonucleotides or deoxynucleotides.

PCT/U.S.92/07678 (WO 93/05183), which is incorporated by reference as if fully set forth herein, teaches a multistep base addition sequencing scheme (BASS) for the rapid sequencing of oligonucleotides (DNA and RNA) involving the steps of attaching a plurality of DNA or RNA strands to be sequenced to a coated support, enzymatically adding a modified nucleotide including a blocking group and a reporter group to the strands, detecting the modified nucleotide via the reporter group, removing the blocking group of the modified nucleotide and repeating these steps until the RNA or DNA is sequenced.

U.S. Pat. No. 5,650,277, which is incorporated by reference as if fully set forth herein, teaches a method aimed at the quantification of di- and trinucleotide repeats in a nucleic acid of interest by (a) if the nucleic acids are not already single stranded, treating a sample containing the nucleic acids of interest to obtain unpaired nucleotide bases spanning the position of the repeats and flanking regions; (b) contacting the unpaired nucleotide bases with an oligonucleotide primer capable of hybridizing with a stretch of nucleotide bases present in the nucleic acid of interest 3' of the trinucleotide repeats to be quantified, so as to form a duplex between the primer and the nucleic acid of interest; (c) ensuring that the examined nucleic acid and the oligonucleotide primer are confined to a reaction chamber at all further steps; (d) contacting the duplex with a primer extension unit which is capable of base pairing with the first nucleotide base in the core sequence of the repeats, and a template dependent extension enzyme; (e) eliminating non-incorporated primer extension units; (f) contacting the template primer duplex with a primer extension unit which is capable of base pairing with the second nucleotide base in the core sequence of the repeats, and a template dependent extension enzyme; (g) eliminating non-incorporated primer extension units; (h) contacting the template primer hybrid with a primer extension unit which is capable of base pairing with the third nucleotide base in the core sequence of the repeats; a detection moiety containing, primer extension unit which is capable of base pairing with a nucleotide base 5' of the repeats region, said nucleotide base being the first nucleotide base of a type not included among the nucleotide bases in the core sequence of the trinucleotide repeats; and a template dependent extension enzyme; (i) eliminating non-incorporated primer extension units; (j) detecting for the presence of detection moiety containing primer extension unit; (k) repeating steps (d) to (j) until detecting the detection moiety. The number of repeats as stated under (k) enables the determination of the number of trinucleotide repeats, therefore enabling determination of the exact repetition number.

However, all of the above methods are highly ineffective or inoperative when sequencing of GC rich sequences, especially sequences containing 100% G+C nucleotides, is attempted due to the formation of stable secondary structures in the nucleic acid being sequenced which hamper the sequential incorporation of nucleotides to a growing chain duplexed thereto.

There is thus a widely recognized need for, and it would be highly advantageous to have, methods and kits for characterizing GC rich nucleic acid sequences devoid of the above limitations.

SUMMARY OF THE INVENTION

According to one aspect of the present invention there is provided a method of characterizing a GC rich region of a nucleic acid of interest comprising the steps of (a) contacting the nucleic acid of interest with an agent that modifies cytosine or guanine residues into residues complementary to adenine or thymine for obtaining a modified nucleic acid in which the cytosine or guanine residues are replaced by the residues complementary to adenine or thymine; (b) amplifying the modified nucleic acid by amplification primers being hybridizable with the modified nucleic acid and being designed for directing exponential amplification of at least a portion of the modified nucleic acid, for obtaining an amplification product corresponding to the GC rich region; and (c) determining the size of the amplification product, thereby characterizing the GC rich region of the nucleic acid of interest.

According to another aspect of the present invention there is provided a kit useful for characterizing a GC rich region of a nucleic acid of interest comprising carrier being compartmentalized to receive in close confinement therein one or more containers comprising a first container containing an agent effective in modifying cytosine or guanine residues of the nucleic acid of interest into residues complementary to adenine or thymine for obtaining a modified nucleic acid in which the cytosine or guanine residues are replaced by the residues complementary to adenine or thymine, a second container or containers containing amplification primers for amplifying the modified nucleic acid the primers being hybridizable with the modified nucleic acid and being designed for directing exponential amplification of at least a portion of the modified nucleic acid, for obtaining an amplification product corresponding to the GC rich region.

According to yet another aspect of the present invention there is provided a method of characterizing a GC rich region of a nucleic acid of interest comprising the steps of (a) contacting the nucleic acid of interest with an agent that modifies cytosine or guanine residues into residues complementary to adenine or thymine for obtaining a modified nucleic acid in which the cytosine or guanine residues are replaced by the residues complementary to adenine or thymine; (b) contacting the modified nucleic acid in a single stranded form with a sequencing primer hybridizeable with a stretch of nucleotides of the single stranded form of the modified nucleic acid; (c) synthesizing a complementary nucleic acid being complementary to the single stranded form of the modified nucleic acid, the synthesizing being carried out in a stepwise serial manner in which the identity of each nucleotide incorporated into the complementary nucleic acid is determined subsequent to its incorporation; and (d) determining a sequence of the single stranded form of the modified nucleic acid, thereby characterizing the GC rich region of the nucleic acid of interest.

According to further features in preferred embodiments of the invention described below, the method further comprising the step of (e) prior to step (b), amplifying the modified nucleic acid by amplification primers being hybridizable with the modified nucleic acid and being designed for directing exponential amplification of at least a portion of the modified nucleic acid, for obtaining an amplification product corresponding to the GC rich region, and using a single stranded form of the amplification product for synthesizing the complementary nucleic acid.

According to still further features in the described preferred embodiments step (c) is effected in four confinements each corresponding to one type of the four nucleotide types present in DNA.

According to still further features in the described preferred embodiments step (c) is effected in a single confinement.

According to still further features in the described preferred embodiments each the nucleotide incorporated into the complementary nucleic acid contains a removable blocking group at its 3'—OH position.

According to still further features in the described preferred embodiments each the nucleotide incorporated into the complementary nucleic acid contains a reporter group.

According to still further features in the described preferred embodiments the reporter group is removable.

According to still further features in the described preferred embodiments the reporter group is selected from the group consisting of radiolabel, fluorolabel, metal ions antibodies and chemiluminesence compounds.

According to still further features in the described preferred embodiments the identity of each nucleotide incorporated into the complementary nucleic acid is determined subsequent to its incorporation by monitoring a release of a PPi group.

According to still further features in the described preferred embodiments monitoring the release of the PPi group is effected by a PPi-detection enzyme.

According to still further features in the described preferred embodiments the method is effective in quantifying the number of trinucleotide repeats having a known core sequence and therefore a known modified core sequence in the nucleic acid of interest, wherein step (c) is effected by the cycled steps of (i) providing a first primer extension unit for base pairing with a first nucleotide base in the known modified core sequence and with a template dependent extension enzyme; (ii) eliminating non-incorporated units of the first primer extension units; (iii) providing a second primer extension unit for base pairing with a second nucleotide base in the known modified core sequence, the second nucleotide base being located adjacent to and immediately 5' of the nucleotide base employed under step (i), and with a template dependent extension enzyme; (iv) eliminating non-incorporated units of the second primer extension units; (v) providing: (a) a third primer extension unit for base pairing with a third nucleotide base in the known modified core sequence, the third nucleotide base being located adjacent to and immediately 5' of the nucleotide base under step (iii); (b) a reporter moiety which is conjugated with a fourth primer extension unit for base pairing with a nucleotide base 5' of the repeats, the nucleotide base being the first nucleotide base of a type not included among the nucleotide bases in the modified core sequence of the trinucleotide repeats, the reporter moiety which is conjugated with the fourth primer extension unit may be present in selected cycles of this stage; and (c) a template dependent extension enzyme; (vi) eliminating non-incorporated units of the third and fourth primer extension units; (vii) if step (v) included the reporter moiety which is conjugated with the fourth primer extension unit, detecting the presence of the reporter moiety; and if no detection is obtained, (viii) repeating steps (i) to (vii) until the reporter moiety is detected, the detection of the reporter moiety being indicative of the number of trinucleotide repeats included in the nucleic acid of interest.

According to further features in preferred embodiments of the invention described below, the kit further comprising a third container containing an additional agent effective in demethylating the GC rich region of the nucleic acid of interest.

According to still further features in the described preferred embodiments the demethylating agent includes a cell lysate, an enzyme or a ribozyme for effecting enzymatic demethylation of the nucleic acid of interest.

According to still further features in the described preferred embodiments the demethylating agent includes a demethylation chemical, for effecting chemical demethylation of the nucleic acid of interest.

According to still further features in the described preferred embodiments each of the amplification primers is GC clamp-free.

According to still further features in the described preferred embodiments the modifying agent is effective in modifying cytosine residues (either methylated or unmethylated) into residues complementary to adenine.

According to still further features in the described preferred embodiments the modifying agent is effective in modifying cytosine residues (either methylated or unmethylated) into residues complementary to thymine.

According to still further features in the described preferred embodiments the modifying agent is effective in modifying guanine residues into residues complementary to adenine.

According to still further features in the described preferred embodiments the modifying agent is effective in modifying guanine into residues complementary to thymine.

According to still further features in the described preferred embodiments the modifying agent is bisulfite which modifies unmethylated cytosine residues into uracil residues.

According to still further features in the described preferred embodiments the kit further comprising a DNA polymerase, preferably, a heat stable DNA polymerase.

According to still further features in the described preferred embodiments the heat stable DNA polymerase is derived from a species selected from the group consisting of *Therinophilus aquaticus, Thermus thermophilus, Pyrococcus furiosus, Thermus flavus, Bacillus stearothermophilus, Thermococcus litoralis* and *Escherichia coli*.

According to still further features in the described preferred embodiments the heat stable DNA polymerase is exonuclease-deficient.

According to still further features in the described preferred embodiments the primers are designed to hybridize 5' to and 3' to a trinucleotide repeat region in the nucleic acid of interest.

According to still further features in the described preferred embodiments trinucleotide repeat region is of a gene associated with a hereditary disease selected from the group consisting of Fragile XA syndrome (FRAXA), spinal and bulbar muscular atrophy (SMBA), myotonic dystrophy (DM), Huntington's disease (HD), spinocerebrellar ataxia type 1 (SCA1), fragile XE mental retardation (FRAXE-MR) and dentatorubral pallidoluysian atrophy (DRAPLA).

The present invention successfully addresses the shortcomings of the presently known configurations by providing methods and kits for characterizing GC rich nucleic acid sequences, such as trinucleotide repeats in cases of, for example, fragile XA (FMR1).

BRIEF DESCRIPTION OF THE DRAWINGS

The invention herein described, by way of example only, with reference to the accompanying drawings, wherein:

FIG. 1 is a schematic depiction of a kit according to the present invention;

FIG. 2 provides an example of a variable region of a FMR1 allele including a repeat structure as follows: $(CGG)_{10}AGG(CGG)_9$, wherein the repeat region is highlighted and FIGS. 3–4 show the different strands of the sequence of FIG. 2, following treatment with SB, as well as the position and sequence of amplification/sequencing primers which can be used for amplification/sequencing of each of the strands.

DESCRIPTION OF THE PREFERRED EMBODIMENT

The present invention is of methods and kits which can be used for characterizing GC rich nucleic acid sequences. Specifically, the present invention can be used for size determination and/or sequencing of GC rich nucleic acid sequences.

The principles and operation of the methods and kits according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of characterizing a GC rich region of a nucleic acid of interest.

In a first step of the method the nucleic acid of interest is contacted with an agent that modifies cytosine or guanine residues into residues complementary to adenine or thymine. Thereby, a modified nucleic acid is obtained, in which the cytosine or guanine residues are replaced by the residues complementary to adenine or thymine.

The nucleic acid of interest is typically derived from an individual to be diagnosed and it is typically genomic DNA or RNA. It may be purified, semi-purified or not purified. It is typically derived from white blood cells of the individual, yet other tissues are also envisaged, especially in the case of RNA. Pretreatment of the nucleic acid of interest prior to bisulfite treatment to limit the size of the treated nucleic acid by either chemical, physical (e.g., shearing) or enzymatic (e.g., sequence specific (restriction enzymes) and sequence non-specific (DNase) treatment) cleavage would assist in achieving more efficient denaturation of the nucleic acid. Before, during and following the treatment with the modifying agent the nucleic acid of interest can be confined to a reaction zone or chamber. For example, the nucleic acid of interest can be bound to a solid support either directly or indirectly (e.g., through a capture oligonucleotide supplemented with an anchoring moiety, as further detailed hereinunder). Confinement of the nucleic acid of interest can otherwise be effected following the teachings of U.S. Pat. Nos. 4,806,313 and 4,921,805, both are incorporated by reference as if fully set forth herein. Confinement as described can assist in maintaining the nucleic acid of interest in a single stranded form, which may results in higher efficiency of the modification process.

In a second step of the method, the modified nucleic acid is amplified by amplification primers (e.g., oligonucleotides). The primers are selected hybridizable with the modified nucleic acid and are designed for directing exponential amplification of at least a portion of the modified nucleic acid, for obtaining an amplification product corresponding to the GC rich region.

As used herein in the specification and in the claims section below the term "primer" refers to a single stranded nucleotide sequence (oligonucleotide) having at least 12, preferably at least 15, more preferably at least 17 or 18, most preferably between 17 and 30 nucleotides, yet longer primers having more than 30 nucleotides are also within the scope of the present invention. Primers according to preferred embodiments of the invention are oligodeoxynucleotides, yet other natural and analog nucleotides (including, for example, protein nucleic acid bases, known as PNA) are also applicable.

In a third step of the method, the size of the amplification product is determined and, as a result, the GC rich region of the nucleic acid of interest is characterized.

Size determination according to the present invention can be effected in a variety of ways, including, but not limited to, gel electrophoresis, dialysis, filtration, gradient centrifugation or any other way of size fractionation. Gel electrophoresis, which is a most sensitive size separation technique for determining the size of an amplification product is presently preferred and can be effected by agarose (and agarose derivatives) gel electrophoresis, polyacrylamide gel electrophoresis, improved MetaPhor gel electrophoresis and capillary electrophoresis.

The migrating amplification product according to the present invention is readily detectable by means of intercalating agents, such as, but not limited to, ethidium bromide propidium iodide and acridine orange. Such agents are known to intercalate into double-stranded DNA molecules. As a result of such intercalation, these agents undergo a change in their spectral properties, such as absorption and fluorescence, which results in a readily detectable radiation attenuation and emission enhancement. Ethidium bromide, for example, has a main absorption (excitation) peak at 510 nm, yet ethidium dimers (homo- and heterodimers) can be excited at 488 nm (argon laser). Thiazolium and oxazolium nucleic acid stains (Molecular Probes Inc.), such as, Yo-Pro-1 and To-PRO-1 are optimally excited by the argon laser. To-PRO-3 is excited by the Hb-Ne laser at 633 nm. These dyes has fluorescence intensity of almost zero, except when they are intercalated in nucleic acids. Benzothiazolium-4-quinolinium dimer (TOTO-1) fluorescence increases about 3000-fold upon binding to DNA or RNA. It is virtually nonfluorescent unless bound to DNA or RNA. TOTO-3 can be excited by the He:Ne laser at 633 nm and the Kr laser at 647 nm. 9-Amino-6-Chloro-2-Methoxyacridine is a DNA intercalator which binds poly[d (A-T)] with Kd of approximately 100 nM. It is excited at 430 nm. Excitation thereof is possible with most light sources. Additional information concerning thiazolium and axazolium nucleic acid stains is provided in the Molecular Probes Inc. catalog.

Alternatively, one or both of the amplification primers or one or more of the nucleoside-tri-phosphate employed for amplification can be labeled, for example, with a directly (e.g., fluorescent) or indirectly (e.g., biotin, antigen, etc.) detectable moiety to effect detection of amplification products. Such a detectable moiety can also serve for separation of amplification products, as well known in the art.

According to another aspect of the present invention there is provided a kit useful for characterizing a GC rich region of a nucleic acid of interest. As shown in FIG. 1, the kit includes a carrier 10 which is compartmentalized to receive in close confinement therein one or more containers 20. A first container contains an agent effective in modifying cytosine or guanine residues of the nucleic acid of interest into residues complementary to adenine or thymine for obtaining a modified nucleic acid in which the cytosine or guanine residues are replaced by the residues complementary to adenine or thymine. A second container or containers contains amplification primers (e.g., oligonucleotides) for amplifying the modified nucleic acid. The primers are selected hybridizable with the modified nucleic acid and are designed for directing exponential amplification of at least a portion of the modified nucleic acid, for obtaining an amplification product corresponding to the GC rich region in the nucleic acid of interest. As further detailed hereinunder, the kit according to the present invention can be used to implement the method of the present invention described hereinabove.

As still further detailed hereinunder, the method and kit hereinabove described are very useful in the analysis of trinucleotide repeat mutations, especially such mutations wherein the core sequence of the repeat includes only G and C residues. As described in the Background section above, such sequences are not readily amplifyable using conventional amplification strategies. Yet, by using the modifying agent as described above, one ensures that the C and/or G nucleotide bases are modified into nucleotide bases complementary with A and/or T nucleotide bases, to thereby obtain the modified nucleic acid in which the G and/or C content is reduced, yet which maintains a similar size. Such a modified sequence is readily amplifyable by conventional sequence amplifying techniques.

The preferred amplification procedure employed according to the present invention when amplifying the modified nucleic acid is the polymerase chain reaction (PCR) which is known to include cycled denaturation, annealing and elongation steps of appropriate temperatures, wherein elongation is effected typically by a thermostable DNA polymerase. Alternative methods of amplification, such as, but not limited to, strand displacement amplification (SDA) and nucleic acid sequence-based amplification (NASBA), have been described and can also be employed.

The amplification products according to the present invention can be sequenced using any conventional electrophoresis based sequencing approach, as well known in the art (see, for example Sanger et al., Proc Natl Acad Sci USA, 1977, 74(12):5463–7; Fuller. Methods Enzymol 1992, 216:329–534; and U.S. Pat. No. 5,432,065.

However, according to another aspect of the present invention there is provided another method of characterizing a GC rich region of a nucleic acid of interest. The method according to this aspect of the present invention is effected by implementing the following method steps, in which, in a first step, the nucleic acid of interest is contacted with an agent that modifies cytosine or guanine residues into residues complementary to adenine or thymine, thereby a modified nucleic acid in which the cytosine or guanine residues are replaced by the residues complementary to adenine or thymine is obtained.

In a second step of the method according to this aspect of the present invention the modified nucleic acid in a single stranded form is contacted with a sequencing primer (e.g., oligonucleotide) hybridizeable with a stretch of nucleotides of the single stranded form of the modified nucleic acid.

In a third step of the method according to this aspect of the present invention a complementary nucleic acid which is complementary to the single stranded form of the modified nucleic acid is synthesized, the synthesis thereof is carried out in a stepwise serial manner in which the identity of each nucleotide incorporated into the complementary nucleic acid is determined subsequent to its incorporation.

In a fourth step of the method according to this aspect of the present invention a sequence of the single stranded form of the modified nucleic acid is determined, thereby the GC rich region of the nucleic acid of interest is characterized at the sequence level.

According to a preferred embodiment of the present invention the modified nucleic acid is amplified by amplification primers prior to the synthesis of the complementary nucleic acid. The amplification primers are selected hybridizable with the modified nucleic acid and are designed for directing exponential amplification of at least a portion of the modified nucleic acid, for obtaining an amplification product corresponding to the GC rich region. A single stranded form of the amplification product is thereafter used as a template for synthesizing the complementary nucleic acid as described above. This is a presently advantageous step because the amplification step can be used to enrich the target nucleic acid to be eventually sequenced by the method.

Electrophoresis-free nucleic acid sequencing approaches are well known in the art and are based on the template dependent stepwise sequential addition of nucleotides to a growing complementary chain, wherein the type of nucleotide added in each step is monitored. One such approach is disclosed in WO9813523A1 to Nyren, Ronaghi et al. (Science, 1998, 281(5375):363, 365, Nyren et al. (Anal Biochem, 1997, 244(2):367–373) Ronaghi et al. (Anal Biochem, 1996, 242(1):84–9) and Nyren et al. (Anal Biochem, 1993, 208(1):171–175), all of which are incorporated by reference as if fully set forth herein. This approach relies on the detection of DNA polymerase activity by an enzymatic luminometric inorganic pyrophosphate (PPi) detection assay (ELIDA) (disclosed in Nyren, Anal Biochem, 1987, 167:235–238, which is incorporated by reference as if fully set forth herein). The PPi formed in the DNA polymerase reaction is converted to ATP by ATP sulfurylase and the ATP production is continuously monitored by, for example, the firefly luciferase, yet other luciferases and other ATP dependent luminescencing proteins are applicable. In the sequencing procedure, immobilized single-stranded template is used in a repeated cycle of deoxynucleotide extension. Real-time signals in the ELIDA, proportional to the amount of incorporated nucleotide, are observed when complementary bases are incorporated. An increased signal-to-noise ratio can be obtained by substitution of deoxyadenosine alpha-thiotriphosphate (dATP alpha S) for the natural deoxyadenosine triphosphate, dATP alpha S is efficiently used by the DNA polymerase, but is not recognized by the luciferase. The reaction is typically performed sequentially in a single confinement, wherein in each cycle a different nucleoside-tri-phosphate or analog is added to the confinement and the luminescence monitored. Additional cycles are performed after carefully washing the confinement ensuring that the template and the complementary nucleic acid growing chain are remained confined in the confinement.

The PPi-detection enzyme(s) according to this embodiment of the present invention are preferably included in the polymerase reaction step and advantageously, in place of deoxy- or dideoxy adenosine triphosphate a is dATP or ddATP analog is used, which is capable of acting as a substrate for a polymerase but incapable of acting as a substrate for said PPi-detection enzyme(s).

PCT/U.S.90/06178 (WO 91/06678) and PCT/U.S.92/07678 (WO 93/05183), both are incorporated by reference as if fully set forth herein describe a different approach for electrophoresis-free sequencing of nucleic acids. In this case nucleotide analogs are employed, each of which includes a removable blocking group and a reporting group, which is also preferably removable. The removable blocking group block the 3'—OH position of the nucleotide and therefore allows for stepwise addition of a single nucleotide at a time in a template dependent fashion to a growing complementary nucleic acid strand. Following such addition, the blocking group is removed so as to leave a free 3'-OH position, so as to permit the addition of the next nucleotide in a template dependent manner. The reporter group serves to inform which nucleotide was incorporated. If four different reporter groups are employed one for each of the nucleotide types, then, the reaction can be performed in a single confinement. If, on the other hand, a single reporter group is employed for all of the nucleotide types, then, four reaction confinements are employed, each one corresponding to one type of the four nucleotide types present in DNA, i.e., A, C, G and T.

Examples of blocking groups and of reporter groups and means for their controlled removal are provided in PCT/U.S.90/06178 (WO 91/06678) and PCT/U.S.92/07678 (WO 93/05183). If the reporter group is removable, then, it can be removed prior to monitoring. If, on the other hand, it is not, then, the commutative effect thereof, or alternatively, the depletion thereof from a reaction mixture due to incorporation can be monitored. Suitable reporter groups include, but are not limited to, radiolabel, fluorolabel, metal ions, antibodies and chemiluminesence compounds.

Another approach of electrophoresis-free nucleic acid sequencing is disclosed in U.S. Pat. No. 5,650,277, which is incorporated by reference as if fully set forth herein. This approach is limited to cases wherein a segment to be sequenced includes di or tri nucleotide repeats and is therefore effective in quantifying the number of trinucleotide repeats having a known core sequence and therefore a known modified core sequence in a nucleic acid of interest. According to this approach a first primer extension unit is provided for base pairing with a first nucleotide base in the known modified core sequence. Non-incorporated units of the first primer extension units are eliminated (e.g., washed out). A second primer extension unit for base pairing with a second nucleotide base in the known modified core sequence is then provided, the second nucleotide base is located adjacent to and immediately 5' of the nucleotide base already employed. Non-incorporated units of the second primer extension units are eliminated. Then, a third primer extension unit for base pairing with a third nucleotide base in the known modified core sequence is provided, along with a reporter moiety which is conjugated with a fourth primer extension unit for base pairing with a nucleotide base 5' of the repeats, this nucleotide base being the first nucleotide base of a type not included among the nucleotide bases in the modified core sequence of the trinucleotide repeats. The reporter moiety which is conjugated with the fourth primer extension unit may be present in selected cycles of this stage. Non-incorporated units of the third and fourth primer extension units are eliminated When applicable, the presence of the reporter moiety is tested. If no detection is obtained, then the above steps are repeated until the reporter moiety is detected. The detection of the reporter moiety is indicative of the number of trinucleotide repeats included in the nucleic acid of interest.

Since every strand conserves information about the sequence of the other strand prior to modification, the original sequence may be deduced by sequencing both strands and using the information to arrive at the original sequence.

In all of the above electrophoresis-free sequencing approaches the template dependent stepwise addition of a nucleotide to a growing complementary nucleic acid chain is effected preferably by a DNA polymerase. Suitable DNA polymerases include, but are not limited to, T7 DNA polymerase, Taq DNA polymerase, Klenow fragment of *E. Coli* DNA polymerase I, *E. Coli* DNA polymerase I, T4 DNA polymerase and, in the template to be sequenced is an RNA template, then reverse transcriptase is preferably employed. A DNA polymerase is also preferably employed in the method of amplifying GC rich nucleic acids according to the present invention. A heat stable (thermostable) DNA polymerase is preferably employed, which is derived from a species, such as, but not limited to, *Thermophilus aquaticus, Thermus thermophilus, Pyrococcus furiosus, Thermus flavus, Bacillus stearothermophilus, Thermococcus litoralis and Escherichia coli*. As used herein, the term "derived" refers both to purified forms and genetically engineered forms of the enzyme employed or portions thereof (e.g., Klenow fragment, either purified or cloned, of *E. coli* DNA polymerase I). The DNA polymerase employed for amplification is preferably exonuclease-deficient.

Restricting an electrophoresis-free sequencing reaction to a confinement is preferable effected according to the present invention by anchoring the template and/or the sequencing primer to a solid support. This can readily be effected by, for example, providing the 5' end of the primer, or an end of the template with a first member of an anchoring pair and further by providing a solid support, e.g., in the form of beads, having their surface coated with a second member of the anchoring pair. The members of the anchoring pairs are selected to have high binding affinity therebetween, so as to effect anchoring of the primer-template duplex to the solid support. Appropriate anchoring pairs, include, but are not limited to, receptor-ligand, antibody-antigen, biotin-avidin, biotin-streptavidin and cellulose binding protein-cellulose.

According to one option of the present invention the modifying agent is effective in modifying cytosine residues (either methylated or unmethylated) into residues complementary to thymine. According to another option of the present invention the modifying agent is effective in modifying guanine residues into residues complementary to adenine.

According to another option of the present invention the modifying agent is effective in modifying guanine into residues complementary to thymine. According to still another option of the present invention the modifying agent is effective in modifying cytosine residues (either methylated or unmethylated) into residues complementary to adenine. The third and fourth options are preferred because according to these options a purine in modified to another purine, whereas a pyrimidine is modified to another pyrimidine. An agent effective in implementing the last option is bisulfite which modifies unmethylated cytosine residues into uracil residues (which are similar to thymine and are complementary to adenine). The use of bisulfite is described in U.S. Pat. No. 5,786,146, which is incorporated by reference as if set forth herein, and which discloses a method of methylation discriminative PCR (MSP), for rapid identification of DNA methylation patterns in a CpG-containing nucleic acid. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by most DNA polymerases. For further detail see Wang et al. Nucleic Acids Res, 1980, 8:4777–4790; Frommer et al. Proc Natl Acad Sci USA, 1992, 89:1827–1831; Clark et al. Nucleic Acids Res, 1994, 22:2990–2997; Raizis et al. Analytical Biochem, 1995, 226:161–166; and Olek et al. Nucleic Acids Research, 1996, 24(24):5064–5066 which are incorporated by reference as if fully set forth herein. Conditions are envisaged, in which the modifying agent bisulfite will effectively interact with both methylated and unmethylated cytosine to modify both such cytosine residues into residues complementary to adenine.

As already mentioned, in many cases genomic DNA is methylated. In higher order eukaryotes, DNA is methylated only at cytosines located 5' to guanosine in a CpG dinucleotide motif or less frequently in a CpNpG trinucleotide motif (Clark at al. Natl Genet, 1995, 10(1):20–7). This modification has important regulatory effects on gene expression, especially when involving CpG rich areas, known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosome of females. Aberrant methylation of normally unmethylated CpG islands has been described as a frequent event in immortalized and transformed cells, and has been associated with transcriptional inactivation of defined tumor suppressor genes in human cancers.

Therefore, according to preferred embodiments of the present invention the kit further includes a third container containing an agent effective in demethylating the GC rich region of the nucleic acid of interest and the amplification and sequencing methods described further include a demethylation step. Demethylation of the DNA is preferably effected prior to the modification thereof with the modifying agent, in both the amplification and sequencing methods according to the present invention. Enzymatic demethylation can be effected by a cell lysate, a demethylase, which is a demethylating enzyme, a demethylating ribozyme or a combination thereof. Alternatively, it can be effected by a demethylating chemical for effecting chemical demethylation.

In vivo demethylation prior to DNA extraction may be carried out by substituting in the growth medium 5-aza-2'-deoxycytidine (5-Aza-CdR) for deoxycytidine (Chiurazzi et al. Human Molecular Genetics, 1998, 7(1):109–113; and Cote et al. Anticancer Drugs, 1998, 9(9):743–50, both are incorporated by reference as if fully set forth herein). This results in the incorporation of this modified nucleotide into the DNA. Since the 5 position of the analog is blocked it cannot undergo methylation. This method is useful only for microorganisms or cell-lines. In vitro DNA demethylation can be effected following the procedures described by Weiss et al. (Cell, 1996, 6;86(5):709–718, which is incorporated by reference as if fully set forth herein) and by Hsieh (Mol Cell Biol, 1999, 19(1):46–56, which is incorporated by reference as if fully set forth herein).

Weiss et al., for example, teach an in vitro system for DNA demethylation using extracts from tissue culture cells. This reaction, which is resistant to proteinase K, takes place through the removal of a 5-methylcytosine nucleotide unit from the DNA substrate.

It will, however, be appreciated that any treatment that would render methylated cytosines susceptible to chemical deamination would be useful as well.

Because of the possible methylation of CpG island in GC-rich regions, some DNA molecules destined to amplification or sequencing according to the present invention may be protected from deamination by sodium bisulfite. One should therefore attempt to choose the amplification and/or sequencing primers such that there would be no CpG dinucleotides in the stretch of nucleotides of the nucleic acid of interest corresponding to the modified nucleic acid hybridizing with the primer, or at least not at or close to the position corresponding to the 3' end of the primer. It may be useful in this respect to use inosine in the primer instead of the G in CpG dinucleotides as this would allow binding of the primer even to non-de aminated and methylated cytosines.

Thus, according to a preferred embodiment of the present invention the primers are designed so that they would be hybridizable to both the modified sequence or to the non-modified sequence. Such primers can include modified nucleotides which allow, or do not interfere with, alternative base pairing. Alternatively, such primers can be degenerated primers, so as to enable at least a fraction of the primers to fully base pair with the target sequence and allow amplification or sequencing thereof as herein described.

According to the present invention each of the amplification primers is GC clamp-free. As used herein in the specification and in the claims section below, the term "GC clamp" refers to a 5' single stranded, template non-related, tailing sequence of between 3 and 150 nucleotides having a 65–100%, preferably 80–100%, more preferably 90–100%, ideally for most cases 100% GC content, added to an oligonucleotide primer. The amplification primers according to preferred embodiments of the present invention are designed to hybridize 5' to and 3' to a trinucleotide repeat region in the nucleic acid of interest.

The present invention can find uses in amplifying and sequencing trinucleotide repeat region in gene associated with a hereditary disease, such as, but not limited to, Fragile XA syndrome (FRAXA), spinal and bulbar muscular atrophy (SMBA), myotonic dystrophy (DM), Huntington's disease (HD), spinocerebrellar ataxia type 1 (SCA1), fragile XE mental retardation (FRAXE-MR) and dentatorubral pallidoluysian atrophy (DRAPLA).

Thus, the present invention is directed at facilitating the amplification and or sequencing of GC-rich amplification-resistant nucleic acid sequences. This is preferably done by treating the genomic DNA from a tested individual with bisulfite in a process that changes every non-methylate cytosine residue in the treated DNA molecule to uracil. This lowers the GC-content of a tested region in the case of Fragile XA, for example, from 100% to about 67%, for one strand, and to about 33% for the other strand. Next, primers that are specific to the tested region, and whose sequences reflect the new (post-treatment) nucleotide sequence are used in the amplification reaction. The result of this treatment is that amplification-resistant DNA sequences are readily amplifyable, using conventional reagents and reaction conditions. One area where such a method would be highly desirable is in the diagnosis of the Fragile X syndrome, where a highly GC rich DNA region in the FMR1 gene precludes the use of PCR in the course of a normal diagnostic procedure.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation and purification. These techniques and various other techniques are generally performed according to Sambrook et al., Molecular Cloning—A Laboratory Manual, Cold Spring Harbor Laboratory, Cold Spring Harbor, N.Y. (1989). Other general references are provided throughout this document. The procedures therein are believed to be well known in the art and are provided for the convenience of the reader. All the information contained therein is incorporated herein by reference.

Example 1

Protocol for Sodium Bisulfite (SB) Treatment of DNA

The following provides a presently preferred protocol treatment for human genomic DNA.

Incubate 20 $\mu$g of human genomic DNA in 50 $\mu$l of 0.3 M NaOH for 15 minutes at 37° C. Bring volume up to 450 $\mu$l with 3.6 M SB (final concentration 3.1 M), then add 25 mM hydroquinone (final concentration of 2.5 mM); mix and incubate at 55° C. for 16 hours under oil.

Purify DNA from the treatment solution (using for example the Gene Clean II kit, Bio 101). Resuspend the pellet in 30 g$\mu$H$_2$O. Add 3 M NaOH to a final concentration of 0.3 M. Incubate for 15 minutes at 37° C. Precipitate DNA using NaOAc and EtOH. Resuspend in 15 $\mu$l H$_2$O.

Example 2

Protocol for PCR Amplification of SB Treated DNA

The following provides an amplification protocol for SB treated DNA.

| Mix: | |
| --- | --- |
| SB treated DNA | 1.0 $\mu$l |
| Upper Primer (10 pmol/$\mu$l) | 5.0 $\mu$l |
| Lower Primer (10 pmol/$\mu$l) | 5.0 $\mu$l |
| dNTPs (2 mM) | 2.5 $\mu$l |
| 10X PCR buffer (-MgCl$_2$) | 2.5 $\mu$l |
| MgCl$_2$ (25 mM) | 1.5 $\mu$l |
| H$_2$O | 7.0 $\mu$l |
| Taq DNA polymerase (2.5 units per $\mu$l) | 0.5 $\mu$l |

Cycle at 94° C., 30 sec., 62° C., 30 sec., 72° C., 60 sec. Employ 35 cycles followed by 5 minutes at 72° C.

Example 3

Amplification of Fragile XA Alleles

Using the above procedure and primers PFX30U (SEQ ID NO:12) and PFX30L (SEQ ID NO:13, see Example 4 below), a 406 bp fragment was amplified from a normal human female DNA sample (29 repeats); a pre mutation DNA sample gave a 440 bp fragment and a control, non-SB treated DNA did not amplify. To prove that the amplified fragments are derived from the expected FMRI region, they were cut with the restriction enzyme SspI and the expected fragments were visualized using agarose gel electrophoresis.

Example 4

Sequencing of a Fragile XA Allele

In the diagnosis of Fragile X syndrome, one determines the mutation state of the FMRI gene by counting or estimating the number of tri-nucleotide repeats therein. The amplification method described herein can be used to render the GC-rich DNA more amenable for amplification. Thereafter known diagnostic methods can be employed, the simplest thereof is sizing of the amplified DNA using, for example, Ethidium bromide stained gels. A change in the repeat number is indicated by the different migration distance of the amplified band. Thus from a woman that is heterozygote for the repeat number, one will amplify, for example, a 304 bp band and a 307 bp band.

Another method for the diagnosis of Fragile X involves conventional (electrophoresis based) DNA sequencing, electrophoresis-free DNA sequencing and the iterative counting of tri-nucleotide repeats, as described in U.S. Pat. No. 5,650,277.

In vitro amplification through the polymerase chain reaction (PCR) or the strand displacement amplification (SDA) and fragment size determination is more easily executed than southern blot analysis and involves fewer steps, these are: (i) amplification of the trinucleotide repeats region using primers from the flanking regions of the repeats; (ii) size determination of amplified fragments through high resolution gel electrophoresis; and (iii) calculation of the number of the trinucleotide repeats. See, Erster, Hum Genet, 1992, 90:55–61. Although this approach is simpler and therefore easier for routine execution, the PCR or SDA approach is not suitable for quantifying highly expanded GC-rich trinucleotide repeats, since its amplifying capacity is limited to relatively small GC-rich fragments.

In cases where the fragment to be amplified exceeds a certain size limit both the PCR and SDA reactions will fail to yield a specific product; and some of the trinucleotide repeats from highly GC rich stretches of DNA (e.g., those found in Fragile X) are not easily amplified by standard amplification protocols.

The following provides an example for sequence analysis of a bisulfite treated DNA.

Assume that the original DNA has the following sequence:

STRAND 1: 5'GCCGATGGA3' (SEQ ID NO:1)
STRAND 2: 3'CGGCTACCT5' (SEQ ID NO:2)

Following bisulfite treatment the modified DNA has the following sequence:

STRAND 1: 5'GUUGATGGA3' (SEQ ID NO:3)
STRAND 2: 3'UGGUTAUUT5' (SEQ ID NO:4)

Since Us and Ts are not readily distinguishable in sequencing reactions and further since following amplification all Us are replaced by Ts, one has to read both sequences and compare them in order to deduce the original sequence.

This can be done as follows:

One aligns the sequences and marks all Us or Ts by X:

STRAND 1: 5'GXXGAXGGA3' (SEQ ID NO:5)
STRAND 2: 3'XGGXXAXXX5' (SEQ ID NO:6)

Xs which opposite Gs are marked (underlined) and reflect Cs in the original sequence, whereas Xs which opposite As are marked (bold) and reflect Ts in the original sequence.

FIG. 2 and SEQ ID NO:7 provide an example of a variable region of a FMR1 allele including a repeat structure as follows: $(CGG)_{10}AGG(CGG)_9$, wherein the repeat region is highlighted.

FIGS. 3–4 and SEQ ID NOs:8–13 show the different strands of the same sequence following treatment with SB, as well as the position and sequence of amplification/sequencing primers which can be used for amplification/sequencing of each of the strands. Thus two sets of amplification primers and two sequencing primers are required for amplifying and sequencing both strands. However, in the case of triple repeats or in a case where only the size is of importance, as opposed to exact sequence, a single set of amplification primers, or a single sequencing primer is required, because the sequence is either predictable or its size, rather than the sequence information contained therein, is of interest.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of characterizing a GC rich region of a nucleic acid of interest comprising the steps of:

(a) demethylating said GC rich region of the nucleic acid of interest;

(b) contacting the nucleic acid of interest with an agent that modifies cytosine or guanine residues into residues complementary to adenine or thymine for obtaining a modified nucleic acid in which said cytosine or guanine residues are replaced by said residues complementary to adenine or thymine;

(c) contacting said modified nucleic acid in a single stranded form with a sequencing primer hybridizeable with a stretch of nucleotides of said single stranded form of said modified nucleic acid;

(d) synthesizing a complementary nucleic acid being complementary to said single stranded form of said modified nucleic acid, said synthesizing being carried out in a stepwise serial manner in which the identity of each nucleotide incorporated into said complementary nucleic acid is determined subsequent to its incorporation; and (e) determining a sequence of said single stranded form of said modified nucleic acid, thereby characterizing said GC rich region of the nucleic acid of interest.

2. The method of claim 1, further comprising the step of:

(f) prior to step (c), amplifying said modified nucleic acid by amplification primers being hybridizable with said modified nucleic acid and being designed for directing amplification of at least a portion of said modified nucleic acid, for obtaining an amplification product corresponding to said GC rich region, and using a single stranded form of said amplification product for synthesizing said complementary nucleic acid.

3. The method of claim 1, wherein step (d) is effected in four confinements each corresponding to one type of the four nucleotide types present in DNA.

4. The method of claim 1, wherein step (d) is effected in a single confinement.

5. The method of claim 1, wherein each said nucleotide incorporated into said complementary nucleic acid contains a removable blocking group at its 3'—OH position.

6. The method of claim 1, wherein each said nucleotide incorporated into said complementary nucleic acid contains a reporter group.

7. The method of claim 6, wherein said reporter group is removable.

8. The method of claim 6, wherein said reporter group is selected from the group consisting of radiolabel, fluorolabel, metal ions antibodies and chemiluminesence compounds.

9. The method of claim 1, wherein said identity of each nucleotide incorporated into said complementary nucleic acid is determined subsequent to its incorporation by monitoring a release of a PPi group.

10. The method of claim 9, wherein monitoring said release of said PPi group is effected by PPi-detection enzymes.

11. The method of claim 1, effective in quantifying the number of trinucleotide repeats having a known core sequence and therefore a known modified core sequence in the nucleic acid of interest, wherein steps (d) and (e) are effected by the cycled steps of:

(i) providing a first nucleotide base unit for base pairing with a first nucleotide base in the known modified core sequence and with a template dependent extension enzyme;

(ii) eliminating non-incorporated base units of said first nucleotide base unit;

(iii) providing a second nucleotide base unit for base pairing with a second nucleotide base in the known modified core sequence, said second nucleotide base being located adjacent to and immediately 5' of the nucleotide base employed under step (i), and with a template dependent extension enzyme;

(iv) eliminating non-incorporated base units of said second nucleotide base unit;

(v) providing:

(a) a third nucleotide base unit for base pairing with a third nucleotide base in the known modified core sequence, said third nucleotide base being located adjacent to and immediately 5' of the nucleotide base under step (iii);

(b) a reporter moiety which is conjugated with a fourth nucleotide base unit for base pairing with a nucleotide base 5' of the repeats, said nucleotide base being the first nucleotide base of a type not included among the nucleotide bases in the modified core sequence of the trinucleotide repeats, said reporter moiety which is conjugated with said fourth nucleotide base unit may be present in selected cycles of this stage; and (c) a template dependent extension enzyme;

(vi) eliminating non-incorporated base units of said third and fourth nucleotide base units;

(vii) if step (v) included said reporter moiety which is conjugated with said fourth nucleotide base unit, detecting the presence of said reporter moiety; and if no detection is obtained, (viii) repeating steps (i) to (vii) until said reporter moiety is detected, said detection of said reporter moiety being indicative of the number of trinucleotide repeats included in the nucleic acid of interest, thereby quantifying the number of trinucleotide repeats in the nucleic acid of interest.

12. The method of claim 1, wherein said demethylation is effected by enzymatic demethylation.

13. The method of claim 1, wherein said demethylation is effected by chemical demethylation.

14. The method of claim 2, wherein each of said amplification primers is GC clamp-free.

15. The method of claim 1, wherein said GC rich region of the nucleic acid of interest includes at least one stretch of nucleotides of at least 9 base pairs which is 100% GC.

16. The method of claim 1, wherein said cytosine residues are modified by said agent into residues complementary to adenine.

17. The method of claim 1, wherein said cytosine residues are modified by said agent into residues complementary to thymine.

18. The method of claim 16, wherein said modifying agent is bisulfite which modifies unmethylated cytosine residues into uracil residues.

19. The method of claim 1, wherein cytosine is modified to uracil.

20. The method of claim 2, wherein amplifying the modified nucleic acid is effected by a polymerase chain reaction (PCR), strand displacement amplification (SDA) or nucleic acid sequence-based amplification (NASBA).

21. The method of claim 1, wherein said CG rich region of the nucleic acid of interest is a trinucleotide repeat.

22. The method of claim 21, wherein said trinucleotide repeat is of a gene associated with a hereditary disease selected from the group consisting of Fragile XA syndrome (FRAXA), spinal and bulbar muscular atrophy (SMBA), myotonic dystrophy (DM), Huntington's disease (HD), spinocerebrellar ataxia type 1 (SCA1), fragile XE mental retardation (FRAXE-MR) and dentatorubral pallidoluysian atrophy (DRAPLA).

23. A method of characterizing a GC rich region of a nucleic acid of interest comprising the steps of:

(a) demethylating said GC rich region of the nucleic acid of interest;

(b) contacting the nucleic acid of interest with an agent that modifies cytosine residues into residues complementary to thymine for obtaining a modified nucleic acid in which said cytosine residues are replaced by said residues complementary to thymine;

(c) contacting said modified nucleic acid in a single stranded form with a sequencing primer hybridizeable with a stretch of nucleotides of said single stranded form of said modified nucleic acid;

(d) synthesizing a complementary nucleic acid being complementary to said single stranded form of said modified nucleic acid, said synthesizing being carried out in a stepwise serial manner in which the identity of each nucleotide incorporated into said complementary nucleic acid is determined subsequent to its incorporation; and (e) determining a sequence of said single stranded form of said modified nucleic acid, thereby characterizing the GC rich region of the nucleic acid of interest.

* * * * *

SEQUENCE LISTING (1) GENERAL INFORMATION:

(iii) NUMBER OF SEQUENCES:13

(2) INFORMATION FOR SEQ ID NO:1:

(i) SEQUENCE CHARACTERISTICS:
      (A) LENGTH:9
      (B) TYPE:nucleic acid
      (C) STRANDEDNESS:double
      (D) TOPOLOGY:linear (xi) SEQUENCE DESCRIPTION: SEQ ID NO:1:

GCCGATGGA                                              9

(2) INFORMATION FOR SEQ ID NO:2:

(i) SEQUENCE CHARACTERISTICS:
      (A) LENGTH:9
      (B) TYPE:nucleic acid
      (C) STRANDEDNESS:double
      (D) TOPOLOGY:linear (xi) SEQUENCE DESCRIPTION: SEQ ID NO:2:

TCCATCGGC                                              9

```
(2) INFORMATION FOR SEQ ID NO:3:

(i) SEQUENCE CHARACTERISTICS:
        (A) LENGTH:9
        (B) TYPE:nucleic acid
        (C) STRANDEDNESS:double
        (D) TOPOLOGY:linear (xi) SEQUENCE DESCRIPTION: SEQ ID NO:3:

GUUGATGGA                                                                  9

(2) INFORMATION FOR SEQ ID NO:4:

(i) SEQUENCE CHARACTERISTICS:
        (A) LENGTH:9
        (B) TYPE:nucleic acid
        (C) STRANDEDNESS:double
        (D) TOPOLOGY:linear (xi) SEQUENCE DESCRIPTION: SEQ ID NO:4:

UGGUTAUUT                                                                  9

(2) INFORMATION FOR SEQ ID NO:5:

(i) SEQUENCE CHARACTERISTICS:
        (A) LENGTH:9
        (B) TYPE:nucleic acid
        (C) STRANDEDNESS:double
        (D) TOPOLOGY:linear (xi) SEQUENCE DESCRIPTION: SEQ ID NO:5:

GNNGANGGA                                                                  9

(2) INFORMATION FOR SEQ ID NO:6:

(i) SEQUENCE CHARACTERISTICS:
        (A) LENGTH:9
        (B) TYPE:nucleic acid
        (C) STRANDEDNESS:double
        (D) TOPOLOGY:linear (xi) SEQUENCE DESCRIPTION: SEQ ID NO:6:

NGGNNANNN                                                                  9

(2) INFORMATION FOR SEQ ID NO:7:

(i) SEQUENCE CHARACTERISTICS:
        (A) LENGTH:700
        (B) TYPE:nucleic acid
        (C) STRANDEDNESS:double
        (D) TOPOLOGY:linear (xi) SEQUENCE DESCRIPTION: SEQ ID NO:7:

CCAGACCAGA CACCCCCTCC CGCGGAATCC CAGAGAGGCC GAACTGGGAT           50

AACCGGATGC ATTTGATTTC CCACGCCACT GAGTGCACCT CTGCAGAAAT          100

GGGCGTTCTG GCCCTCGCGA GGCAGTGCGA CCTGTCACCG CCCTTCAGCC          150

TTCCCGCCCT CCACCAAGCC CGCGCACGCC CGGCCCGCGC GTCTGTCTTT          200

CGACCCGGCA CCCCGGCCGG TTCCCAGCAG CGCGCATGCG CGCGCTCCCA          250

GGCCACTTGA AGAGAGAGGG CGGGGCCGAG GGGCTGAGCC CGCGGGGGGA          300

GGGAACAGCG TTGATCACGT GACGTGGTTT CAGTGTTTAC ACCCGCAGCG          350

GGCCGGGGGT TCGGCCTCAG TCAGGCGCTC AGCTCCGTTT CGGTTTCACT          400

TCCGGTGGAG GGCCGCCTCT GAGCGGGCGG CGGGCCGACG GCGAGCGCGG          450
```

| | |
|---|---|
| GCGGCGGCGG TGACGGAGGC GCCGCTGCCA GGGGGCGTGC GGCAGCGCGG | 500 |
| CGGCGGCGGC GGCGGCGGCG GCGGCGGAGG CGGCGGCGGC GGCGGCGGCG | 550 |
| GCGGCGGCTG GGCCTCGAGC GCCCGCAGCC CACCTCTCGG GGGCGGGCTC | 600 |
| CCGGCGCTAG CAGGGCTGAA GAGAAGATGG AGGAGCTGGT GGTGGAAGTG | 650 |
| CGGGGCTCCA ATGGCGCTTT CTACAAGGTA CTTGGCTCTA GGGCAGGCCC | 700 |

(2) INFORMATION FOR SEQ ID NO:8:

(i) SEQUENCE CHARACTERISTICS:
        (A) LENGTH:700
        (B) TYPE:nucleic acid
        (C) STRANDEDNESS:single
        (D) TOPOLOGY:linear (xi) SEQUENCE DESCRIPTION: SEQ ID NO:8:

| | |
|---|---|
| UUAGAUUAGA UAUUUUUTUU UGUGGAAUUU UAGAGAGGUU GAAUUGGGAT | 50 |
| AAUUGGAUGU AUTTGAUUTU UUAUGUUAUT GAGUGUAUUT UUGUAGAAAT | 100 |
| GGGUGUUUTG GUUUTGUGA GGUAGUGUGA UUGUUAUUG UUUTUAGUU | 150 |
| TTUUUGUUUT UUAUUAAGUU UGUGUAUGUU UGGUUUGUGU GTUTGTUTTT | 200 |
| UGAUUUGGUA UUUUGGUUGG TTUUUAGUAG UGUGUAUGUG UGUGUUUUA | 250 |
| GGUUAUUUGA AGAGAGAGGG UGGGGUUGAG GGGUUGAGUU UGUGGGGGGA | 300 |
| GGGAAUAGUG UUGAUUAUGT GAUGUGGUUU UAGUGUUUAU AUUUGUAGUG | 350 |
| GGUUGGGGGT TUGGUUUUAG TUAGGUGUTU AGUUUGUUU UGGUUUUAUT | 400 |
| TUUGGUGGAG GGUUGUUTUT GAGUGGGUGG UGGGUUGAUG GUGAGUGUGG | 450 |
| GUGGUGGUGG TGAUGGAGGU GUUGUUGUUA GGGGUGUGU GGUAGUGUGG | 500 |
| UGGUGGUGGU GGUGGUGGUG GUGGUGGAGG UGGUGGUGGU GGUGGUGUG | 550 |
| GUGGUGGUTG GGUUUGAGU GUUUGUAGUU UAUUTUTUGG GGGUGGGUTU | 600 |
| UUGGUGUAG UAGGGUGAA GAGAAGAUGG AGGAGUGGU GGTGGAAGTG | 650 |
| UGGGGUUUA AUGGUGUTT UUAUAAGGTA UTTGGUUTA GGGUAGGUU | 700 |

(2) INFORMATION FOR SEQ ID NO:9:

(i) SEQUENCE CHARACTERISTICS:
        (A) LENGTH:18
        (B) TYPE:nucleic acid
        (C) STRANDEDNESS:single
        (D) TOPOLOGY:linear (xi) SEQUENCE DESCRIPTION: SEQ ID NO:9:

| | |
|---|---|
| TGGTGGTGAT GGAGGTGT | 18 |

(2) INFORMATION FOR SEQ ID NO:10:

(i) SEQUENCE CHARACTERISTICS:
        (A) LENGTH:22
        (B) TYPE:nucleic acid
        (C) STRANDEDNESS:single
        (D) TOPOLOGY:linear (xi) SEQUENCE DESCRIPTION: SEQ ID NO:10:

| | |
|---|---|
| TCCATCTTCT CTTCAACCCT AC | 22 |

(2) INFORMATION FOR SEQ ID NO:11:

(i) SEQUENCE CHARACTERISTICS:
        (A) LENGTH:700
        (B) TYPE:nucleic acid
        (C) STRANDEDNESS:single
        (D) TOPOLOGY:linear (xi) SEQUENCE DESCRIPTION: SEQ ID NO:11:

```
GGGUUTGUUU TAGAGUUAAG TAUUTTGTAG AAAGUGUUAT TGGAGUUUUG           50
UAUTTUUAUU AUUAGUTUUT UUATUTTUTU TTUAGUUUTG UTAGUGUUGG          100
GAGUUUGUUU UUGAGAGGTG GGUTGUGGGU GUTUGAGGUU UAGUUGUUGU          150
UGUUGUUGUU GUUGUUGUUG UUTUUGUUGU UGUUGUUGUU GUUGUUGUUG          200
UUGUGUTGUU GUAUGUUUUU TGGUAGUGGU GUUTUUGTUA UUGUUGUUGU          250
UUGUGUTUGU UGTUGGUUUG UUGUUUGUTU AGAGGUGGUU UTUUAUUGGA          300
AGTGAAAUUG AAAUGGAGUT GAGUGUUTGA UTGAGGUUGA AUUUUUGGUU          350
UGUTGUGGGT GTAAAUAUTG AAAUUAUGTU AUGTGATUAA UGUTGTTUUU          400
TUUUUUUGUG GGUTUAGUUU UTUGGUUUUG UUUTUTUTUT TUAAGTGGUU          450
TGGGAGUGUG UGUATGUGUG UTGUTGGGAA UUGGUUGGGG TGUUGGGTUG          500
AAAGAUAGAU GUGUGGGUUG GGUGTGUGUG GGUTTGGTGG AGGGUGGGAA          550
GGUTGAAGGG UGGTGAUAGG TUGUAUTGUU TUGUGAGGGU UAGAAUGUUU          600
ATTTUTGUAG AGGTGUAUTU AGTGGUGTGG GAAATUAAAT GUATUUGGTT          650
ATUUUAGTTU GGUUTUTUTG GGATTUUGUG GGAGGGGGTG TUTGGTUTGG          700
```

(2) INFORMATION FOR SEQ ID NO:12:

(i) SEQUENCE CHARACTERISTICS:
        (A) LENGTH:19
        (B) TYPE:nucleic acid
        (C) STRANDEDNESS:single
        (D) TOPOLOGY:linear (xi) SEQUENCE DESCRIPTION: SEQ ID NO:12:

```
TGGGTTGTGG GTGTTTGAG                                            19
```

(2) INFORMATION FOR SEQ ID NO:13:

(i) SEQUENCE CHARACTERISTICS:
        (A) LENGTH:21
        (B) TYPE:nucleic acid
        (C) STRANDEDNESS:single
        (D) TOPOLOGY:linear (xi) SEQUENCE DESCRIPTION: SEQ ID NO:13:

```
CACCCAACCC ACACATCTAT C                                         21
```